(12) United States Patent
Gilmanshin et al.

(10) Patent No.: US 10,161,926 B2
(45) Date of Patent: Dec. 25, 2018

(54) ACOUSTIC METHODS FOR SEPARATION OF CELLS AND PATHOGENS

(71) Applicant: FloDesign Sonics, Inc., Wilbraham, MA (US)

(72) Inventors: Rudolf Gilmanshin, Framingham, MA (US); Bart Lipkens, Hampden, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 204 days.

(21) Appl. No.: 15/180,015

(22) Filed: Jun. 11, 2016

(65) Prior Publication Data

US 2016/0363579 A1    Dec. 15, 2016

Related U.S. Application Data

(60) Provisional application No. 62/174,512, filed on Jun. 11, 2015.

(51) Int. Cl.
*B01D 43/00* (2006.01)
*G01N 33/49* (2006.01)
(Continued)

(52) U.S. Cl.
CPC ......... *G01N 33/491* (2013.01); *B01D 21/283* (2013.01); *B01D 43/00* (2013.01);
(Continued)

(58) Field of Classification Search
CPC ...... C12M 47/02; C12M 29/18; C12M 29/10; C12M 33/08; C12M 35/04; C12N 13/00;
(Continued)

(56) References Cited

U.S. PATENT DOCUMENTS 2,473,971 A    6/1949    Ross
2,667,944 A    2/1954    Crites
(Continued)

FOREIGN PATENT DOCUMENTS

DE    30 27 433 A1    2/1982
DE    196 48 519 A1    6/1998
(Continued)

OTHER PUBLICATIONS

Alvarez et al.; Shock Waves, vol. 17, No. 6, pp. 441-447, 2008.
(Continued)

*Primary Examiner* — Walter D. Griffin
*Assistant Examiner* — Cameron J Allen
(74) *Attorney, Agent, or Firm* — Richard M. Klein, Esq.; Fay Sharpe, LLP

(57) ABSTRACT

Devices and methods for inspecting, detecting, isolating, monitoring, characterizing, or separating pathogens in blood containing blood cells are disclosed. The devices include a flow chamber having a solvent inlet, at least one host-fluid inlet, a particulate outlet, at least one residual outlet, and a reflector. The methods include trapping the pathogens in the acoustic standing wave, introducing a solvent into the flow chamber, and removing the pathogens from the device. Devices and methods for inspecting, detecting, isolating, monitoring, characterizing, or separating specialized circulating cells in blood containing blood cells are also disclosed. The devices include a flow chamber having at least one inlet and at least one outlet, and a microscope objective and a cover glass. The methods include driving the transducer to create an acoustic standing wave in the flow chamber and microbubbles in the blood.

35 Claims, 9 Drawing Sheets

(51) Int. Cl.

| | |
|---|---|
| *C12Q 1/24* | (2006.01) |
| *G01N 33/574* | (2006.01) |
| *B01L 3/00* | (2006.01) |
| *B06B 1/06* | (2006.01) |
| *B01D 21/28* | (2006.01) |
| *B03B 1/04* | (2006.01) |
| *G01N 15/14* | (2006.01) |
| *A61M 1/36* | (2006.01) |
| *G01N 15/10* | (2006.01) |

(52) U.S. Cl.
CPC ... *B01L 3/502715* (2013.01); *B01L 3/502761* (2013.01); *B03B 1/04* (2013.01); *B06B 1/0622* (2013.01); *C12Q 1/24* (2013.01); *G01N 15/1404* (2013.01); *G01N 15/1436* (2013.01); *G01N 15/1463* (2013.01); *G01N 15/1484* (2013.01); *G01N 33/574* (2013.01); *A61M 1/362* (2014.02); *A61M 1/3678* (2014.02); *B01L 2200/025* (2013.01); *B01L 2200/0647* (2013.01); *B01L 2300/0867* (2013.01); *B01L 2300/0877* (2013.01); *B01L 2400/0436* (2013.01); *G01N 2015/1006* (2013.01); *G01N 2015/149* (2013.01)

(58) Field of Classification Search
CPC .......... C12N 1/02; B01D 17/04; B01D 17/06; B01D 21/283; B01D 29/115; B01D 37/00; B01D 29/52; B01D 29/865; B01D 2201/0415; B01D 2201/0446; B01D 2201/127; B06B 1/0644; H01L 41/0973; C01F 1/46
See application file for complete search history.

(56) References Cited

U.S. PATENT DOCUMENTS

| | | |
|---|---|---|
| 3,372,370 A | 3/1968 | Cyr |
| 3,555,311 A | 1/1971 | Weber |
| 4,055,491 A | 10/1977 | Porath-Furedi |
| 4,065,875 A | 1/1978 | Srna |
| 4,118,649 A | 10/1978 | Schwartzman et al. |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,320,659 A | 3/1982 | Lynnworth et al. |
| 4,344,448 A | 8/1982 | Potts |
| 4,398,325 A | 8/1983 | Piaget et al. |
| 4,666,595 A | 5/1987 | Graham |
| 4,673,512 A | 6/1987 | Schram |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Wang |
| 4,821,838 A | 4/1989 | Chen |
| 4,836,684 A | 6/1989 | Javorik et al. |
| 4,878,210 A | 10/1989 | Mitome |
| 4,983,189 A | 1/1991 | Peterson et al. |
| 5,164,094 A | 11/1992 | Stuckart |
| 5,225,089 A | 7/1993 | Benes et al. |
| 5,371,729 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,484,537 A | 1/1996 | Whitworth |
| 5,527,460 A | 6/1996 | Trampler et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,902,489 A | 5/1999 | Yasuda et al. |
| 5,912,182 A | 6/1999 | Coakley et al. |
| 5,951,456 A | 9/1999 | Scott |
| 6,090,295 A | 6/2000 | Raghavarao et al. |
| 6,166,231 A | 12/2000 | Hoeksema |
| 6,216,538 B1 | 4/2001 | Yasuda et al. |
| 6,205,848 B1 | 6/2001 | Faber et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,482,327 B1 | 11/2002 | Mod et al. |
| 6,487,095 B1 | 11/2002 | Malik et al. |
| 6,592,821 B1 | 7/2003 | Wada et al. |
| 6,649,069 B2 | 11/2003 | DeAngelis |
| 6,699,711 B1 | 3/2004 | Hahn et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,837,040 B2 | 11/2010 | Ward et al. |
| 7,846,382 B2 | 12/2010 | Strand et al. |
| 7,968,049 B2 | 6/2011 | Takahashi et al. |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,392 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,873,051 B2 | 10/2014 | Kaduchak et al. |
| 8,889,388 B2 | 11/2014 | Wang et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2006/0037915 A1* | 2/2006 | Strand .................. B01D 21/283 210/748.05 |
| 2007/0272618 A1 | 11/2007 | Gou et al. |
| 2007/0284299 A1 | 12/2007 | Xu et al. |
| 2008/0067128 A1 | 3/2008 | Hoyos et al. |
| 2008/0105625 A1 | 5/2008 | Rosenberg et al. |
| 2008/0217259 A1* | 9/2008 | Siversson ........... A61M 1/3693 436/177 |
| 2008/0245709 A1 | 10/2008 | Kaduchak et al. |
| 2008/0272034 A1 | 11/2008 | Ferren et al. |
| 2008/0272065 A1 | 11/2008 | Johnson |

(56) References Cited

U.S. PATENT DOCUMENTS

| | | |
|---|---|---|
| 2009/0029870 A1 | 1/2009 | Ward et al. |
| 2009/0045107 A1 | 2/2009 | Ward et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0178716 A1 | 7/2009 | Kaduchak et al. |
| 2009/0194420 A1 | 8/2009 | Mariella, Jr. et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Wienand et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0163126 A1 | 6/2012 | Campbell et al. |
| 2012/0175012 A1 | 7/2012 | Goodwin et al. |
| 2012/0267288 A1 | 10/2012 | Chen et al. |
| 2012/0325727 A1 | 12/2012 | Dionne et al. |
| 2012/0325747 A1 | 12/2012 | Rietman et al. |
| 2012/0328477 A1 | 12/2012 | Dionne et al. |
| 2012/0329122 A1 | 12/2012 | Lipkens et al. |
| 2013/0115664 A1 | 5/2013 | Khanna et al. |
| 2013/0175226 A1 | 7/2013 | Coussios et al. |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2014/0011240 A1* | 1/2014 | Lipkens .............. B01D 21/28 435/71.1 |
| 2014/0017758 A1 | 1/2014 | Kniep et al. |
| 2014/0329997 A1* | 11/2014 | Kennedy, III ......... C07K 1/145 530/388.1 |
| 2015/0053561 A1 | 2/2015 | Ward et al. |

FOREIGN PATENT DOCUMENTS

| | | |
|---|---|---|
| DE | 10 2008 006 501 A1 | 9/2008 |
| EP | 0 292 470 B | 11/1988 |
| EP | 1 254 669 B1 | 11/2002 |
| GB | 2 420 510 A | 5/2006 |
| JP | 9-136090 | 5/1997 |
| WO | WO 1987/07178 A1 | 12/1987 |
| WO | WO 90/05008 | 3/1990 |
| WO | WO 98/50133 A1 | 11/1998 |
| WO | WO 02/072234 A1 | 9/2002 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/131947 A2 | 10/2011 |
| WO | WO 2011/161463 A2 | 12/2011 |
| WO | WO 2013/043297 A1 | 3/2013 |
| WO | WO 2013/055517 A1 | 4/2013 |
| WO | WO 2014/014941 A1 | 1/2014 |
| WO | WO 2014/055219 A2 | 4/2014 |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.

Castro; Tunable gap and quantum quench dynamics in bilayer graphene; Jul. 13, 2010; Mathematica Summer School.

Cravotto et al.; Ultrasonics Sonochemistry, vol. 15, No. 5, pp. 898-902, 2008.

Garcia-Lopez, et al; Enhanced Acoustic Separation of Oil-Water Emulsion in Resonant Cavities. The Open Acoustics Journal. 2008, vol. 1, pp. 66-71.

Hill et al.; Ultrasonic Particle Manipulation; Microfluidic Technologies for Miniaturized Analysis Systems, Jan. 2007, pp. 359-378.

Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.

Lipkens et al.; Frequency sweeping and fluid flow effects on particle trajectories in ultrasonic standing waves; Acoustics 08, Paris, Jun. 29-Jul. 4, 2008.

Lipkens et al.; Prediction and measurement of particle velocities in ultrasonic standing waves; J. Acoust. Soc. Am., 124 No. 4, pp. 2492 (A) 2008.

Lipkens et al.; Separation of micron-sized particles in macro-scale cavities by ultrasonic standing waves; Presented at the International Congress on Ultrasonics, Santiago; Jan. 11-17, 2009.

Lipkens et al.; The effect of frequency sweeping and fluid flow on particle trajectories in ultrasonic standing waves; IEEE Sensors Journal, vol. 8, No. 6, pp. 667-677, 2008.

Lipkens et al., Macro-scale acoustophoretic separation of lipid particles from red blood cells, The Journal of the Acoustical Society of America, vol. 133, Jun. 2, 2013, p. 045017, XP055162509, New York, NY.

Meribout et a.; An Industrial-Prototype Acoustic Array for Real-Time Emulsion Layer Detection in Oil Storage Tanks; IEEE Sensors Journal, vol. 9, No. 12, Dec. 2009.

Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.

Pangu et al.; Droplet transport and coalescence kinetics in emulsions subjected to acoustic fields; Ultrasonics 46, pp. 289-302 (2007).

Ponomarenko et al.; Density of states and zero Landau level probed through capacitance of graphene; Nature Nanotechnology Letters, Jul. 5, 2009; DOI: 10.1038/NNANO.2009.177.

Seymour et al, J. Chem. Edu., 1990, 67(9), p. 763, published Sep. 1990.

Wang et al.; Retention and Viability Characteristics of Mammalian Cells in an Acoustically Driven Polymer Mesh; Biotechnol. Prog. 2004, pp. 384-387 (2004).

Annex to Form PCT/ISA/206—Communication Relating to the Results of the Partial International Search Report, dated Jul. 18, 2013.

European Search Report of European Application No. 11769474.5, dated Oct. 10, 2012.

European Search Report of European Application No. 13760840.2, dated Feb. 4, 2016.

(56) References Cited

OTHER PUBLICATIONS

International Search Report and Written Opinion dated Dec. 20, 2011, for corresponding PCT application No. PCT/US2011/032181.
International Search Report and Written Opinion dated Feb. 27, 2012, for PCT application No. PCT/US2011/040787.
International Search Report and Written Opinion of International Application No. PCT/US2012/051804 dated Nov. 16, 2012.
International Search Report and Written Opinion of International Application No. PCT/US2013/037404 dated Jun. 21, 2013.
International Search Report and Written Opinion of International Application No. PCT/US2013/032705 dated Jul. 26, 2013.
International Search Report and Written Opinion of International Application No. PCT/US2013/050729 dated Sep. 25, 2013.
International Search Report dated Feb. 18, 2014 in corresponding PCT Application No. PCT/US2013/059640.
International Search Report for corresponding PCT Application Serial No. PCT/US2014/015382 dated May 6, 2014.
International Search Report for PCT/US2014/035557 dated Aug. 27, 2014.
International Search Report for PCT/US2014/043930 dated Oct. 22, 2014.
International Search Report for PCT/US2014/046412 dated Oct. 27, 2014.
International Search Report for PCT/US2014/064088 dated Jan. 30, 2015.
Extended European Search Report for Application No. EP 12833859.7 dated Mar. 20, 2015.
International Search Report and Written Opinion for International Application No. PCT/US2015/010595 dated Apr. 15, 2015.
International Search Report for PCT/US2015/019755 dated May 4, 2015.
International Search Report dated Jul. 30, 2015 for International Application No. PCT/US2015/030009.
International Search Report for PCT/US2015/039125 dated Sep. 30, 2015.
European Search Report of European Application No. 11796470.0 dated Jan. 5, 2016.
Phys. Org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>.
International Search Report and Written Opinion for International Application No. PCT/US2016/037104 dated Dec. 16, 2016.

\* cited by examiner

ACOUSTIC METHODS FOR SEPARATION OF CELLS AND PATHOGENS

CROSS-REFERENCE TO RELATED APPLICATIONS

This application claims priority to U.S. Provisional Patent Application Ser. No. 62/174,512, filed on Jun. 11, 2015, the disclosure of which is hereby fully incorporated by reference in its entirety.

BACKGROUND

The identification and separation of specialized circulating cells, such as circulating tumor cells (CTCs) or pathogenic cells such as *Escherichia coli* (*E. coli*) is very desirable for advancing the knowledge of cancer types, for diagnostics, and for monitoring the progress of cancer treatments.

One conventional method of identifying and separating specialized circulating cells utilizes different fluorescent materials to tag different cells based on their specific surface chemistry. The cells are then sorted based on their different fluorescent colors. This method, however, attaches secondary molecules to the cell of interest and may modify the surface characteristics of the cells, which is undesirable. Other methods of locating rare cells in circulation involve video or microscopy techniques, which are painstaking and very time-consuming processes.

Diagnostic applications for specialized circulating cells typically require the ability to be used with small analysis volumes. In addition, reagents for such applications are very expensive. Because only a small number of target cells are contained in the specimen and they are at low concentrations, high sensitivity (i.e. the ability to correctly identify the target cells) and high specificity (i.e. the ability to correctly identify cells that are not the target cells) are desirable.

It would therefore be desirable to provide methods for both identification and segmentation or separation of rare cell types for both diagnostic and treatment purposes. A ready-to-operate system for both identification and segmentation or separation of rare cell types for both diagnostic and treatment purposes is likewise desirable. Diagnostic systems and methods that enhance sensitivity are desirable, in addition to systems and method with high specificity, as incorrect identification causes incorrect or unnecessary treatment.

BRIEF DESCRIPTION

The present disclosure relates, in various embodiments, to systems and methods of identification and separation of target cells such as specialized circulating cells and/or rare cell types, such as pathogenic cells, utilizing acoustic manipulation via acoustic standing waves. These systems and methods are useful for various diagnostic and treatment purposes, including pathogen detection in blood, and trapping and characterization of specialized circulating cells, such as CTCs. Briefly, the use of an acoustic standing allows for contact-free manipulation of cells, thereby increasing sensitivity because of the elimination of contact with surfaces, which are the main channel of losses of cells and reagents. Additionally, acoustic manipulation allows for high local concentrations of analytes at large microfluidic volumes, which enhances sensitivity, lowers costs, and simplifies the design. Finally, the acoustic manipulation systems and methods described herein advantageously possess the potential for automation of the manipulation of particles or cells through the combination of fluid flows and acoustic pressure using an acoustic standing wave.

In accordance with the present disclosure, methods are disclosed for inspecting, detecting, isolating, monitoring, characterizing, or separating pathogens from a fluid (e.g. in blood or its derivatives, containing blood cells). The method comprises flowing the fluid containing the pathogens through an acoustic manipulation device. The fluid may be diluted, such as up to ten times its original concentration. The fluid may also be stratified through the use of a centrifuge and then separated prior to introduction into the acoustic separation device. The stratified layers may be treated separately. For example, in blood, one typically stratified layer is known as the "buffy coat" and contains the white cells and platelets in the blood sample. The white cells are neutrophils, eosinophils, basophils, lymphocytes, and monocytes. The lymphocytes can contain T cells, B cells and NK cells. The acoustic manipulation device comprises a flow chamber having a solvent inlet and at least one host-fluid inlet at a first end of the flow chamber, and a particulate outlet and at least one residual outlet at a second end of the flow chamber opposite the first end thereof, wherein the solvent inlet and the particulate outlet are aligned with a longitudinal axis of the flow chamber and the at least one host-fluid inlet and the at least one residual outlet are spaced apart from the longitudinal axis; at least one ultrasonic transducer located on a wall of the flow chamber, the at least one ultrasonic transducer including a piezoelectric material driven by a voltage signal to create an acoustic standing wave in the flow chamber; and a reflector located on a wall on the opposite side of the flow chamber from the at least one ultrasonic transducer. The flow chamber may alternatively be shaped to form a resonant chamber. The method further comprises sending a voltage signal to drive the at least one ultrasonic transducer to create the acoustic standing wave in the flow chamber to drive the pathogens toward the longitudinal axis where the pathogens become trapped in the acoustic standing wave; introducing a solvent into the flow chamber through the solvent inlet; and removing the pathogens from the device through the particulate outlet.

In particular embodiments, the acoustic manipulation device further comprises at least one buffer inlet located between the solvent inlet and the at least one host-fluid inlet. The method may further comprise introducing a buffer into the flow chamber through the at least one buffer inlet, the buffer creating a buffer layer that permits the pathogens to pass therethrough but destroys other cells as they pass therethrough. The buffer can be a selective lytic buffer (e.g., mild detergents). Alternatively, an osmotic shock can be employed to create the buffer layer. If cells (e.g., mammalian cells) are passed through a solvent having a low salt concentration, the cells are generally caused to explode while the bacteria survives due to its cellular walls. Note that for acoustical purposes, the change of the density due to the decrease of salt concentration could be compensated with agents that can increase the solvent density without changing its osmolality (e.g., Ficoll, Histodenz).

The method may further comprise removing the solvent from the device through the residual outlet. The solvent may be a bacteria-friendly solvent (e.g., saline, culture broth).

In certain constructions, the piezoelectric material can include a plurality of piezoelectric elements arranged in an array, the plurality of piezoelectric elements operated between active and inactive modes such that the pathogens are trapped above the piezoelectric elements in the active mode. The method may further comprise switching the piezoelectric elements between the active and inactive modes to move the pathogens trapped in the acoustic standing wave along the longitudinal axis from the first end to the second end of the flow chamber to the particulate outlet.

According to the present disclosure, another method is disclosed for inspecting, detecting, isolating, or characterizing specialized circulating cells (e.g., CTCs, stem cells, CAR T cells) in a host fluid containing the targeted cells (e.g. blood containing blood cells). The method comprises flowing the host fluid containing the targeted cells through an acoustic manipulation device. The acoustic manipulation device comprises a flow chamber having at least one inlet and at least one outlet; at least one ultrasonic transducer located on a wall of the flow chamber, the at least one ultrasonic transducer including a piezoelectric material driven by a voltage signal to create an acoustic standing wave in the flow chamber; and a transparent wall forming a wall of the flow chamber opposite the at least one ultrasonic transducer. In certain embodiments, a cover glass may be required for high-resolution, high-sensitivity detection employing oil-immersed objectives. In other embodiments, objectives with lower magnification and long working distance may not require a cover glass. The method further comprises sending a voltage signal to drive the at least one ultrasonic transducer to create the acoustic standing wave in the flow chamber, and attaching acoustically active particles (e.g., microbubbles or paramagnetic particles having an affinity ligand attached) to the specialized circulating cells, the acoustically active particles being driven by the acoustic standing wave toward the transparent wall where the specialized circulating cells and attached microbubbles become trapped in the acoustic standing wave. A microscope objective is used to examine the cells through the transparent wall.

In particular embodiments, the at least one inlet includes a solvent inlet and at least one host-fluid inlet at a first end of the flow chamber, and the at least one outlet includes a particulate outlet and at least one residual outlet at a second end of the flow chamber opposite the first end thereof, wherein the solvent inlet and the particulate outlet are aligned with a longitudinal axis of the flow chamber and the at least one host-fluid inlet and the at least one residual outlet are spaced apart from the longitudinal axis.

The acoustic manipulation device may further comprise at least one buffer inlet located between the solvent inlet and the at least one host-fluid inlet. The method may further comprise introducing a dividing buffer into the flow chamber through the at least one buffer inlet. A substantially acoustically transparent layer may be present between the cover glass and the flow chamber. The substantially acoustically transparent layer can include one or more wells therein.

The piezoelectric material may include a plurality of piezoelectric elements arranged in an array, the plurality of piezoelectric elements configured to operate between active and inactive modes such that the targeted cells are trapped above the piezoelectric elements in the active mode. The method may further comprise switching the piezoelectric elements between the active and inactive modes to position the targeted cells trapped in the acoustic standing wave in alignment with the microscope objective. The substantially acoustically transparent layer can include one or more wells therein. The method may further comprise switching the piezoelectric elements between the active and inactive modes to position the targeted cells trapped in the acoustic standing wave in the wells of the substantially acoustically transparent layer.

The targeted cells can be specialized circulating cells, such as circulating tumor cells.

Acoustophoretic devices are also disclosed. In one embodiment, an acoustophoretic device comprises a flow chamber having a solvent inlet and at least one host-fluid inlet at a first end of the flow chamber, and a particulate outlet and at least one residual outlet at a second end of the flow chamber opposite the first end thereof, wherein the solvent inlet and the particulate outlet are aligned with a longitudinal axis of the flow chamber and the at least one host-fluid inlet and the at least one residual outlet are spaced apart from the longitudinal axis; at least one ultrasonic transducer located on a wall of the flow chamber, the at least one ultrasonic transducer including a piezoelectric material driven by a voltage signal to create an acoustic standing wave in the flow chamber; and a reflector located on a wall on the opposite side of the flow chamber from the at least one ultrasonic transducer.

In particular embodiments, the acoustophoretic device further comprises at least one buffer inlet located between the solvent inlet and the at least one host-fluid inlet.

The piezoelectric material may include a plurality of piezoelectric elements arranged in an array, the plurality of piezoelectric elements configured to operate between active and inactive modes.

The flow chamber can be disposable.

In certain constructions, the at least one ultrasonic transducer comprises a housing having a top end, a bottom end, and an interior volume; and a piezoelectric crystal at the bottom end of the housing having an exposed exterior surface and an interior surface, the crystal being able to vibrate when driven by a voltage signal. In some embodiments, no backing layer is present within the housing of the at least one ultrasonic transducer, and an air gap is present in the interior volume between the crystal and a top plate at the top end of the housing. In other embodiments, the at least one ultrasonic transducer further comprises a backing layer contacting the interior surface of the crystal, the backing layer being made of a substantially acoustically transparent material.

In a second embodiment, an acoustophoretic device comprises a flow chamber having at least one inlet and at least one outlet; at least one ultrasonic transducer located on a wall of the flow chamber, the at least one ultrasonic transducer including a piezoelectric material driven by a voltage signal to create an acoustic standing wave in the flow chamber; and a transparent wall forming a portion of the flow chamber opposite the at least one ultrasonic transducer. The flow chamber may also or alternatively include a transducer and a resonant chamber, with no specific reflector component opposite the transducer.

In particular embodiments, the at least one inlet includes a solvent inlet and at least one host-fluid inlet at a first end of the flow chamber, and the at least one outlet includes a particulate outlet and at least one residual outlet at a second end of the flow chamber opposite the first end thereof, wherein the solvent inlet and the particulate outlet are aligned with a longitudinal axis of the flow chamber and the at least one host-fluid inlet and the at least one residual outlet are spaced apart from the longitudinal axis.

The acoustophoretic device may further comprise at least one buffer inlet located between the solvent inlet and the at least one host-fluid inlet. A substantially acoustically transparent layer may be present between the transparent wall and the interior volume of the flow chamber.

The piezoelectric material may include a plurality of piezoelectric elements arranged in an array, the plurality of piezoelectric elements configured to operate between active and inactive modes.

The flow chamber can be disposable.

In certain constructions, the at least one ultrasonic transducer comprises a housing having a top end, a bottom end, and an interior volume; and a piezoelectric crystal at the bottom end of the housing having an exposed exterior surface and an interior surface, the crystal being able to vibrate when driven by a voltage signal. In some embodiments, no backing layer is present within the housing of the at least one ultrasonic transducer, and an air gap is present in the interior volume between the crystal and a top plate at the top end of the housing. In other embodiments, the at least one ultrasonic transducer further comprises a backing layer contacting the interior surface of the crystal, the backing layer being made of a substantially acoustically transparent material.

In particular embodiments of the methods and devices according to the present disclosure, the acoustic standing wave may be a multi-dimensional acoustic standing wave. Examples of such multi-dimensional acoustic standing waves can be found in commonly owned U.S. Pat. No. 9,228,183, the entire contents being hereby fully incorporated by reference. In other embodiments of the methods and devices according to the present disclosure, the acoustic standing wave can be a planar acoustic standing wave. Further yet, in particular embodiments, the acoustic standing wave may be a combination of a planar acoustic standing wave and a multi-dimensional acoustic standing wave, where the planar acoustic standing wave and multidimensional acoustic standing wave are super positioned on each other.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
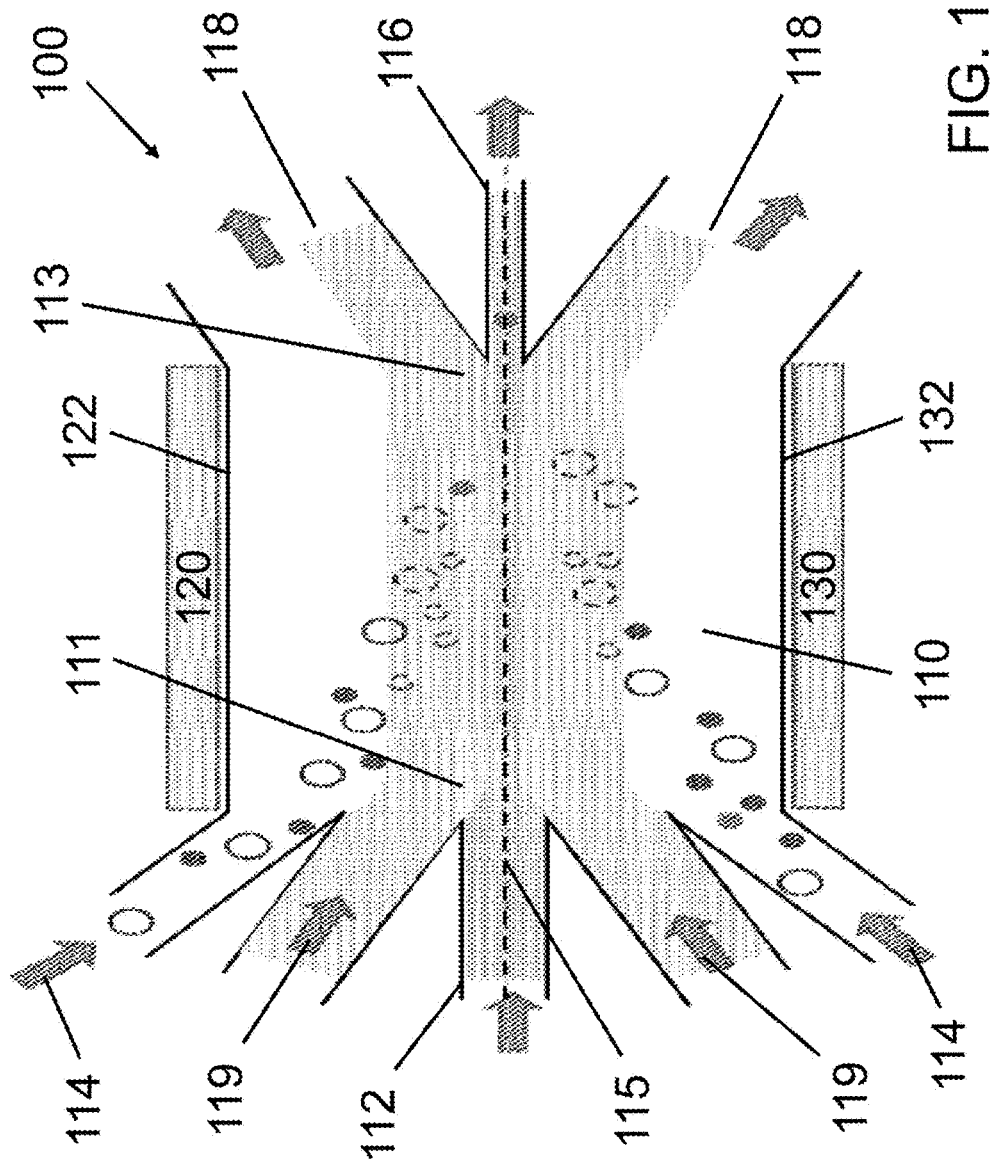
FIG. 1 is a plan view of a first exemplary embodiment of an acoustophoretic device according to the present disclosure. The device includes a flow chamber having a solvent inlet, at least one host-fluid inlet, a particulate outlet, at least one residual outlet, and at least one buffer inlet.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of from about 2 to about 10% also discloses the range "from 2 to 10." The term "about" may refer to plus or minus 10% of the indicated number. For example, "about 10%" may indicate a range of 9% to 11%, and "about 1" may mean from 0.9-1.1.

It should be noted that many of the terms used herein are relative terms. For example, the terms "upper" and "lower"

are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth.

The term "parallel" should be construed in its lay sense of two surfaces that maintain a generally constant distance between them, and not in the strict mathematical sense that such surfaces will never intersect when extended to infinity.

The present application refers to "the same order of magnitude." Two numbers are of the same order of magnitude if the quotient of the larger number divided by the smaller number is a value of at least 1 and less than 10.

Acoustophoresis is the separation of particles and secondary fluids from a primary or host fluid using high intensity acoustic standing waves, and without the use of membranes or physical size exclusion filters. It has been known that high intensity standing waves of sound can exert forces on particles in a fluid when there is a differential in both density and/or compressibility, otherwise known as the acoustic contrast factor. The pressure profile in a standing wave contains areas of local minimum pressure amplitudes at its nodes and local maxima at its anti-nodes. Depending on the density and compressibility of the particles, they will be trapped at the nodes or anti-nodes of the standing wave. Generally, the higher the frequency of the standing wave, the smaller the particles that can be trapped due the pressure of the standing wave.

When acoustic standing waves propagate in liquids, the fast oscillations may generate a non-oscillating force on particles suspended in the liquid or on an interface between liquids. This force is known as the acoustic radiation force. The force originates from the non-linearity of the propagating wave. As a result of the non-linearity, the wave is distorted as it propagates and the time-averages are nonzero. By serial expansion (according to perturbation theory), the first non-zero term will be the second-order term, which accounts for the acoustic radiation force. The acoustic radiation force on a particle, or a cell, in a fluid suspension is a function of the difference in radiation pressure on either side of the particle or cell. The physical description of the radiation force is a superposition of the incident wave and a scattered wave, in addition to the effect of the non-rigid particle oscillating with a different speed compared to the surrounding medium thereby radiating a wave. The following equation presents an analytical expression for the acoustic radiation force on a particle, or cell, in a fluid suspension in a planar standing wave.

$$F_R = \frac{3\pi P_0^2 V_P \beta_m}{2\lambda} \varphi(\beta, \rho)\sin(kx) \quad (1)$$

where $\beta_m$ is the compressibility of the fluid medium, $\rho$ is density, $\varphi$ is acoustic contrast factor, $V_p$ is particle volume, $\lambda$ is wavelength, k is $2\pi/\lambda$, $P_0$ is acoustic pressure amplitude, x is the axial distance along the standing wave (i.e., perpendicular to the wave front), and $$\varphi(\beta, \rho) = \frac{5\rho_p - 2\rho_m}{2\rho_p + \rho_m} - \frac{\beta_p}{\beta_m}$$

where $\rho_p$ is the particle density, $\rho_m$ is the fluid medium density, $\beta_p$ is the compressibility of the particle, and $\beta_m$ is the compressibility of the fluid medium.

For a multi-dimensional standing wave, the acoustic radiation force is a three-dimensional force field, and one method to calculate the force is Gor'kov's method, where the primary acoustic radiation force $F_R$ is defined as a function of a field potential U, $F_V = -\nabla(U)$, where the field potential U is defined as $$U = V_0 \left[ \frac{\langle p^2(x, y, t) \rangle}{2\rho_f c_f^2} f_1 - \frac{3\rho_f \langle v^2(x, y, t) \rangle}{4} f_2 \right]$$

and $f_1$ and $f_2$ are the monopole and dipole contributions defined by $$f_1 = 1 - \frac{1}{\Lambda\sigma^2} \quad f_2 = \frac{2(\Lambda - 1)}{2\Lambda + 1},$$

where $$\sigma = \frac{c_p}{c_f} \quad \Lambda = \frac{\rho_p}{\rho_f} \quad \beta_f = \frac{1}{\rho_f c_f^2}$$

where $\rho$ is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o$ is the volume of the cell, and $<>$ indicates time averaging over the period of the wave.

The present disclosure relates to acoustophoretic devices and methods that employ multi-dimensional ultrasonic acoustic standing waves, planar acoustic standing waves or combinations of planar and multidimensional acoustic standing waves (collectively referred to herein simple as acoustic standing waves) to separate cells and/or other particles from the fluid surrounding them. This can be useful for diagnostic applications.

The acoustophoretic or acoustically active devices of the present disclosure can be used for the extraction of bacteria from a mixture of bacteria and cells (e.g., mammalian cells). Examples of other applications of the acoustophoretic devices of the present disclosure include detecting contamination of cell cultures or for separation of impurities from fluids in the food and beverage industry. The acoustophoretic or acoustically active devices of the present disclosure can also be used to diagnose and treat blood infections. For example, a volume of blood (e.g., 10 milliliters) drained from a patient can be split into two separate samples for bacteria and yeast detection. Half of the blood is then injected into an appropriate culture bottle and submitted to a blood culturing system (e.g., BACTEC) for growth. Once the pathogens in the blood grow to sufficient concentration, a sample aliquot is then analyzed by a matrix-assisted laser desorption/ionization time-of-flight mass spectrometer (MALDI-TOF MS). The typical pathogen concentration is about one to two pathogens per milliliter. Thus, for a five milliliter blood sample in a 50 milliliter bottle, the sample begins with about five to ten pathogens. Growth in the blood culturing system is generally complete at about $10^6$ to about $10^7$ pathogens per milliliter, which takes about 20 to 24 generations, or about 10 to 12 hours. Generally, the volume of sample required for mass spectrometry is about 1 microliter. Time-to-answer is critical in blood infections, because the more developed sepsis becomes, the more difficult it is to treat the infection, and the progressing bacteremia can induce septic shock.

FIGS. 1-5 illustrate various embodiments of acoustophoretic devices according to the present disclosure.

In particular, FIG. 1 illustrates a first exemplary embodiment of an acoustophoretic device 100. The device 100 includes a flow chamber 110, at least one ultrasonic transducer 120, and a reflector 130.

The flow chamber 110 is the region of the device 100 through which is flowed the fluid sample, containing both mammalian and bacterial cells (e.g., blood containing blood cells and bacteria, yeast, or specialized circulating cells), or more generally, the host fluid contains both target cells (to be separated from the host fluid) and non-target cells (which are to remain with the host fluid). The flow chamber 110 includes a solvent inlet 112, at least one host-fluid inlet 114, a particulate outlet 116, at least one residual outlet 118, and at least one buffer inlet 119.

The solvent inlet 112, the at least one host-fluid inlet 114, and the at least one buffer inlet 119 are located at a first end 111 of the flow chamber 110. The at least one buffer inlet 119 is located between the solvent inlet 112 and the at least one host-fluid inlet 114. The particulate outlet 116 and the at least one residual outlet 118 are located at a second end 113 of the flow chamber 110. As seen in FIG. 1, the first end 111 of the flow chamber 110 is opposite the second end 113 of the flow chamber 110. As can also be seen from FIG. 1, the solvent inlet 112 and the particulate outlet 116 are aligned with a longitudinal axis 115 of the flow chamber 110, and the at least one host-fluid inlet 114, the at least one buffer inlet 119, and the at least one residual outlet 118 are spaced apart from the longitudinal axis 115.

In the embodiment of FIG. 1, the device 100 includes one solvent inlet 112, two host-fluid inlets 114, a particulate outlet 116, two residual outlets 118, and two buffer inlets 119. In this regard, it is noted that the flow chamber 110 of device 100 is reflectionally symmetrical about the longitudinal axis 115.

The ultrasonic transducer 120 of the device 100 is located on wall 122 of the flow chamber 110. The reflector 130 of the device 100 is located on wall 132 of the flow chamber 110. As seen in FIG. 1, wall 132 is located on the opposite side of the flow chamber 110 from wall 122, such that the reflector 130 is located on an opposite side of the flow chamber 110 from the ultrasonic transducer 120. In this way, one or more acoustic standing waves are created in the flow chamber between the ultrasonic transducer and the reflector. Each node of the acoustic standing wave(s) is generally sheathed with layers of the solvent, such that the number of acoustic standing waves created in the flow chamber may correspond to the number of outlets of the device.

Prior to discussing further optimization of the systems, it is helpful to provide an explanation now of how multi-dimensional acoustic standing waves are generated. The multi-dimensional acoustic standing wave is obtained by driving an ultrasonic transducer at a frequency that both generates the acoustic standing wave and excites a fundamental 3D vibration mode of the transducer piezoelectric element. Perturbation of the piezoelectric element in an ultrasonic transducer in a multimode fashion allows for generation of a multidimensional acoustic standing wave. A piezoelectric element can be specifically designed to deform in a multimode fashion at designed frequencies, allowing for generation of a multi-dimensional acoustic standing wave. The multi-dimensional acoustic standing wave may be generated by distinct modes of the piezoelectric element such as a 3×3 mode that would generate multidimensional acoustic standing waves. A multitude of multidimensional acoustic standing waves may also be generated by allowing the piezoelectric element to vibrate through many different mode shapes. Thus, the element would excite multiple modes such as a 0×0 mode (i.e. a piston mode) to a 1×1, 2×2, 1×3, 3×1, 3×3, and other higher order modes and then cycle back through the lower modes of the element (not necessarily in straight order). This switching or dithering of the element between modes allows for various multi-dimensional wave shapes, along with a single piston mode shape, to be generated over a designated time.

It is also possible to excite or choose a frequency of excitation that excites multiple modes at the same time, each mode with a varying degree of displacement amplitude. Through this combination of multiple modes excited at the same time with varying displacement amplitude, it is possible to generate a superposition of multi-dimensional standing waves desirable for trapping, clustering, and separation of a secondary fluid or particle from a host fluid.

The scattering of the acoustic field off the particles results in a three dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). When the acoustic radiation force exerted on the particles is stronger than the combined effect of fluid drag force and buoyancy and gravitational force, the particles are trapped within the acoustic standing wave field. This can result in the concentration, agglomeration and/or coalescence of the trapped particles depending on the type of acoustic standing wave that is utilized. Relatively large solids of one material can thus be separated from smaller particles of a different material, the same material, and/or the host fluid through enhanced gravitational separation.

The multi-dimensional standing wave generates acoustic radiation forces in both the axial direction (i.e., in the direction of the standing wave, between the transducer and the reflector, perpendicular to the flow direction) and the lateral direction (i.e., in the flow direction). As the mixture flows through the acoustic chamber, particles in suspension experience a strong axial force component in the direction of the standing wave. Since this acoustic force is perpendicular to the flow direction and the drag force, it quickly moves the particles to pressure nodal planes or anti-nodal planes, depending on the contrast factor of the particle. The lateral acoustic radiation force then acts to move the concentrated particles towards the center of each planar node, resulting in agglomeration or clumping. The lateral acoustic radiation force component has to overcome fluid drag for such clumps of particles to continually grow. Therefore, both the drop in drag per particle as the particle cluster increases in size, as well as the drop in acoustic radiation force per particle as the particle cluster grows in size, must be considered for the acoustic separator device to work effectively. In the present disclosure, the lateral force component and the axial force component of the multi-dimensional acoustic standing wave are of the same order of magnitude. In this regard, it is noted that in a multi-dimensional acoustic standing wave, the axial force is stronger than the lateral force, but the lateral force of a multi-dimensional acoustic standing wave is much higher than the lateral force of a planar standing wave, usually by two orders of magnitude or more.

Figure 2:
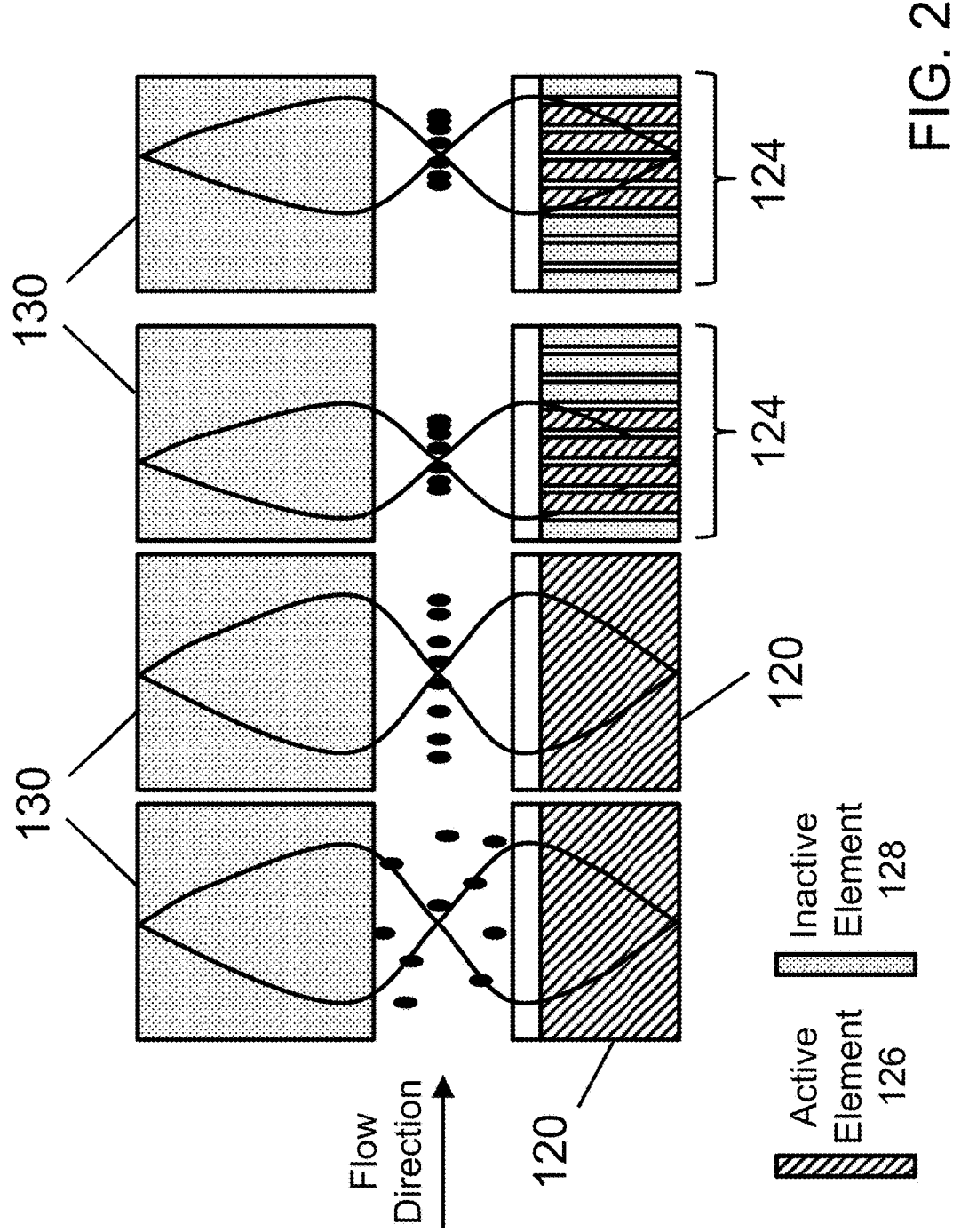
FIG. 2 illustrates several exemplary transducer-reflector arrangements according to the present disclosure.

FIG. 2 illustrates several exemplary transducer-reflector arrangements. Beginning on the left side of FIG. 2, particles or cells are shown scattered between a transducer 120 and reflector 130. As seen in the second illustration from the left, the transducer can be driven so as to cause the particles or cells to collect, agglomerate, aggregate, clump, or coalesce at the nodes or anti-nodes of the acoustic standing wave, depending on the particles' or secondary fluid's acoustic contrast factor relative to the host fluid. Turning now to the third and fourth illustrations from the left in FIG. 2, the ultrasonic transducer 120 is shown as including a plurality of piezoelectric elements 124 arranged in an array. The plurality of piezoelectric elements are configured to operate in active or inactive modes, as depicted. Piezoelectric elements in the active mode are generally considered to be "on," such that particles or cells are trapped above those elements, while elements in the inactive mode are generally considered to be "off," with no particle trapping occurring above those elements. The individual piezoelectric elements may be of any suitable size and shape. In certain embodiments, the piezoelectric elements may be smaller than the size of the objects to be trapped or moved between the active piezoelectric elements. The piezoelectric elements can be individually switched between the active and inactive modes as desired. For example, in the third illustration from the left in FIG. 2, elements 1 and 6-8 are operated in the inactive mode and elements 2-5 are operated in the active mode, such that the particles or cells are trapped above elements 2-5 (i.e., towards the left end of the flow chamber). In comparison, in the rightmost illustration in FIG. 2, elements 1-3 and 8 are operated in the inactive mode and elements 4-7 are operated in the active mode, such that the particles or cells are trapped above elements 4-7 (i.e., towards the right end of the flow chamber). In this way, switching between which elements are active/inactive can be used to move the trapped particles or cells from one end of the flow chamber to another (i.e., sweeping the trapped particles or cells) or to align the trapped particles or cells in desired locations within the flow chamber.

The acoustophoretic devices of the present disclosure are operable to perform acoustics-driven selective lysis with microfluidic separation, thereby concentrating pathogens and holding them for growth. The acoustophoretic devices, such as that depicted in FIG. 1, can be further used for elution, monitoring pathogen growth, and/or inspecting, detecting, isolating, monitoring, characterizing, or separating pathogens (e.g., bacteria, yeast, E. coli, lymphocytes) in blood containing blood cells. The blood containing pathogens and blood cells is flowed through the acoustophoretic device. As explained above, a voltage signal is sent to drive the at least one ultrasonic transducer to create the acoustic standing wave in the flow chamber. As explained above and depicted in the transducer-reflector arrangements in FIG. 2, the acoustic standing wave drives the pathogens toward the longitudinal axis where the bacteria become trapped in the acoustic standing wave and can be walked towards the particulate outlet. A solvent (e.g., a bacteria-friendly solvent) is then introduced into the flow chamber through the solvent inlet. Finally, the pathogens are removed from the device through the particulate outlet.

Figure 3:
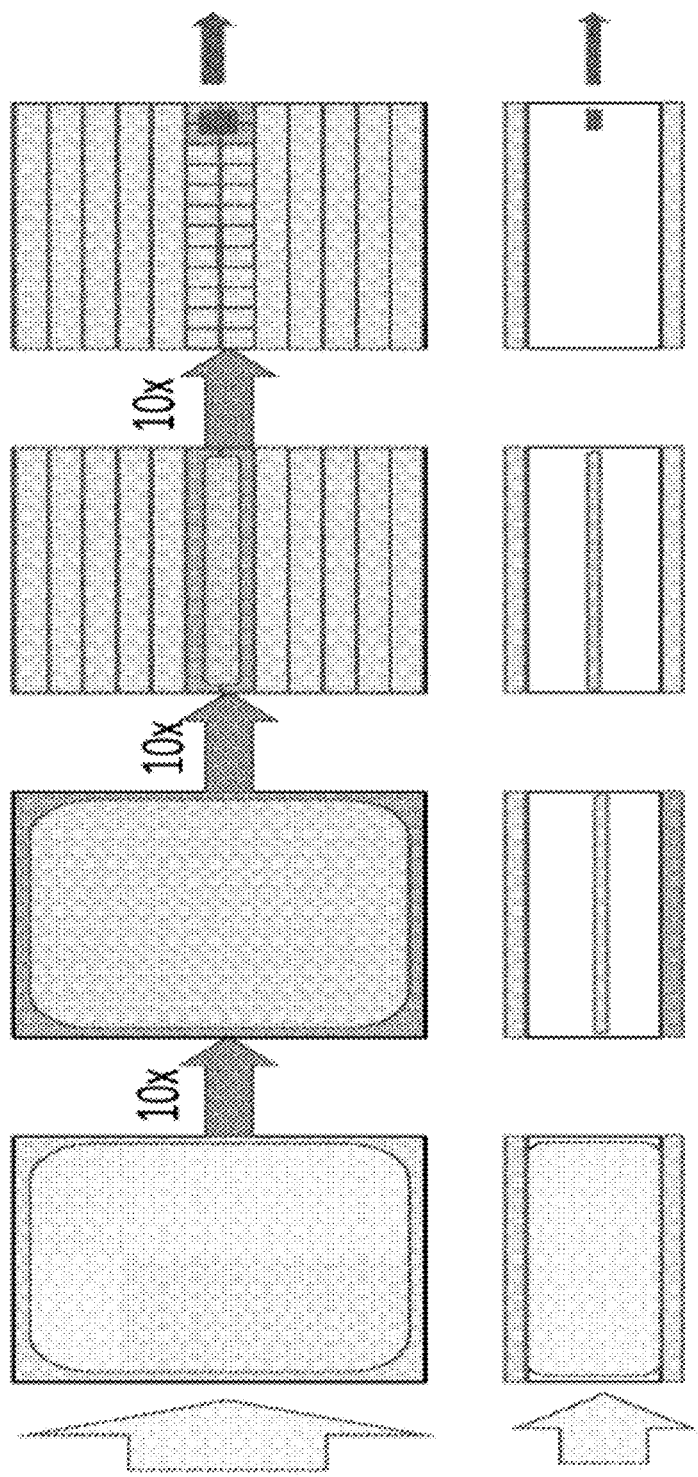
FIG. 3 illustrates an acoustic concentrator according to the present disclosure.

When the acoustophoretic device is provided with a buffer inlet, a buffer (e.g., a dividing buffer or a selective lytic buffer) can be introduced into the flow chamber through the at least one buffer inlet. The buffer generally creates a buffer layer in the flow chamber that permits the pathogens to pass therethrough but destroys the specimen (e.g., blood cells) as it passes therethrough. This may also be called differential lysis. In FIG. 1, the buffer layer is depicted in the flow chamber 110 by gray shading. As can be further seen in FIG. 1, the blood cells in the blood (depicted as large white circles) become destroyed upon interfacing with the buffer layer, while the pathogens in the blood (depicted as smaller black circles) pass into the buffer layer and are driven toward the longitudinal axis by the acoustic standing wave. The pathogens may be eventually removed from the device via the particulate outlet. By selecting flow pressures and channel cross-sections, a concentrating factor of 10 or higher can be achieved. The fluid compression generates a concentrating factor of 10, while the acoustic compression generates a concentrating factor of $10^3$, through use of an acoustic concentrator, such as the acoustic concentrator described below and shown in FIG. 3. As shown in FIG. 3, three consecutive acoustic ten-fold compressions along three axes normal to each other provide the $10^3$ concentrating factor. Constructing the acoustic concentrator with piezoelectric elements arranged in an array allows for concentrated cells in elution to be transported out of the concentrator. In certain embodiments, the acoustic concentrator can be operated with all of the piezoelectric elements in the active mode (i.e., "on" as shown in the bottom half of FIG. 3), which is useful for retaining the cells in the concentrator during culture broth circulation. This construction further permits the injection of larger volumes than the resonator volume, thereby providing an additional concentrating factor. Due to this combined $10^4$ concentrating factor, all cells from a five millimeter sample can be compressed into a 0.5 microliter sample, which is sufficient for mass spectrometry. Further concentration is also possible by injecting larger volumes into the system, while acoustically retaining the cells using the acoustic standing wave. In comparison to currently-employed processes, the presently disclosed methods require less than 10 division cycles due to the smaller total volume and less than 0-4 division cycles due to growth monitoring, with division cycles of 0.5 hours or more, which may be shortened relative to the blood culturing system due to the circulating culture broth.

Figure 4:
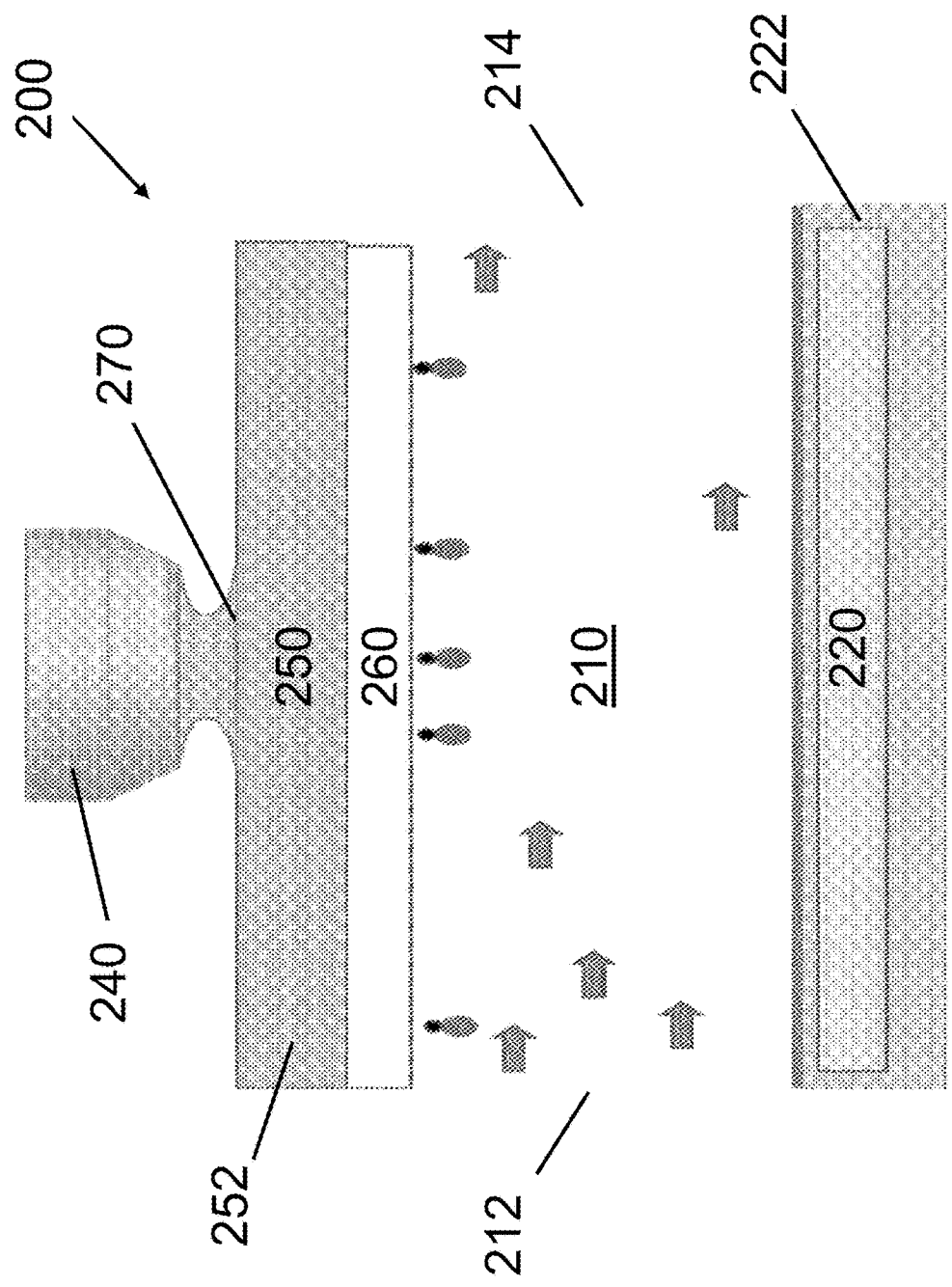
FIG. 4 is a plan view of a second exemplary embodiment of an acoustophoretic device according to the present disclosure. The device includes a transducer located opposite an acoustically transparent layer and an optically transparent wall. A microscope objective can examine cells within the flow chamber of the device through the optically transparent wall.

Turning now to FIG. 4, a second exemplary embodiment of an acoustophoretic device 200 is depicted.

The device 200 includes a flow chamber 210, at least one ultrasonic transducer 220, a transparent wall 250, and an optional acoustically transparent layer 260. A microscope objective 240 is illustrated here, which can be used to characterize the cells within the flow chamber.

The flow chamber 210 is the region of the device 200 through which is flowed a host fluid containing target cells. The flow chamber 210 includes at least one inlet 212 and at least one outlet 214. The at least one inlet 210 may include a solvent inlet, at least one host-fluid inlet, and optionally include at least one buffer inlet as shown and described above with respect to device 100. Likewise, the at least one outlet 214 may include a particulate outlet and at least one residual outlet as shown and described above with respect to device 100.

The ultrasonic transducer 220 of the device 200 is located on wall 222 of the flow chamber 210. The microscope objective 240 of the device 200 is located on the opposite side of the flow chamber 210 from the ultrasonic transducer 220. The optically transparent wall 250 is located between the microscope objective 240 and the flow chamber 210 volume, and forms wall 252 of the flow chamber 210. As seen in FIG. 4, wall 252 is located on the opposite side of the flow chamber 210 from wall 222 (i.e., on the same side as the microscope objective 240), such that the microscope objective 240 and the transparent wall 250 are located on the same side of the flow chamber 210 opposite from the ultrasonic transducer 220. In this way, one or more acoustic standing waves are created in the flow chamber between the ultrasonic transducer 220 and the transparent wall 250. The use of an ultrasonic transducer without an opposite reflector may be herein referred to as a "one-piece acoustic radiator." It is noted that walls 222, 252 of the flow chamber can be made from the same material, or can be made from different materials. The wall 252 should be optically transparent (i.e. can see through it), but wall 222 does not have to be transparent.

Generally, the microscope objective 240 is used to inspect or monitor the target cells trapped within the flow chamber 210. In certain embodiments, such as that shown in FIG. 4, an immersion oil layer 270 may be provided between the microscope objective 240 and the optically transparent wall 250. Further yet, an acoustically transparent layer 260 may be present between the cover glass 250 and the flow chamber 210. The acoustically transparent layer (ATL) prevents the cells from being pressed against the glass surface. The ATL may be a hydrogel. This surface may be advantageous for certain stem cells that can be studied with the system described in FIG. 4.

Figure 5:
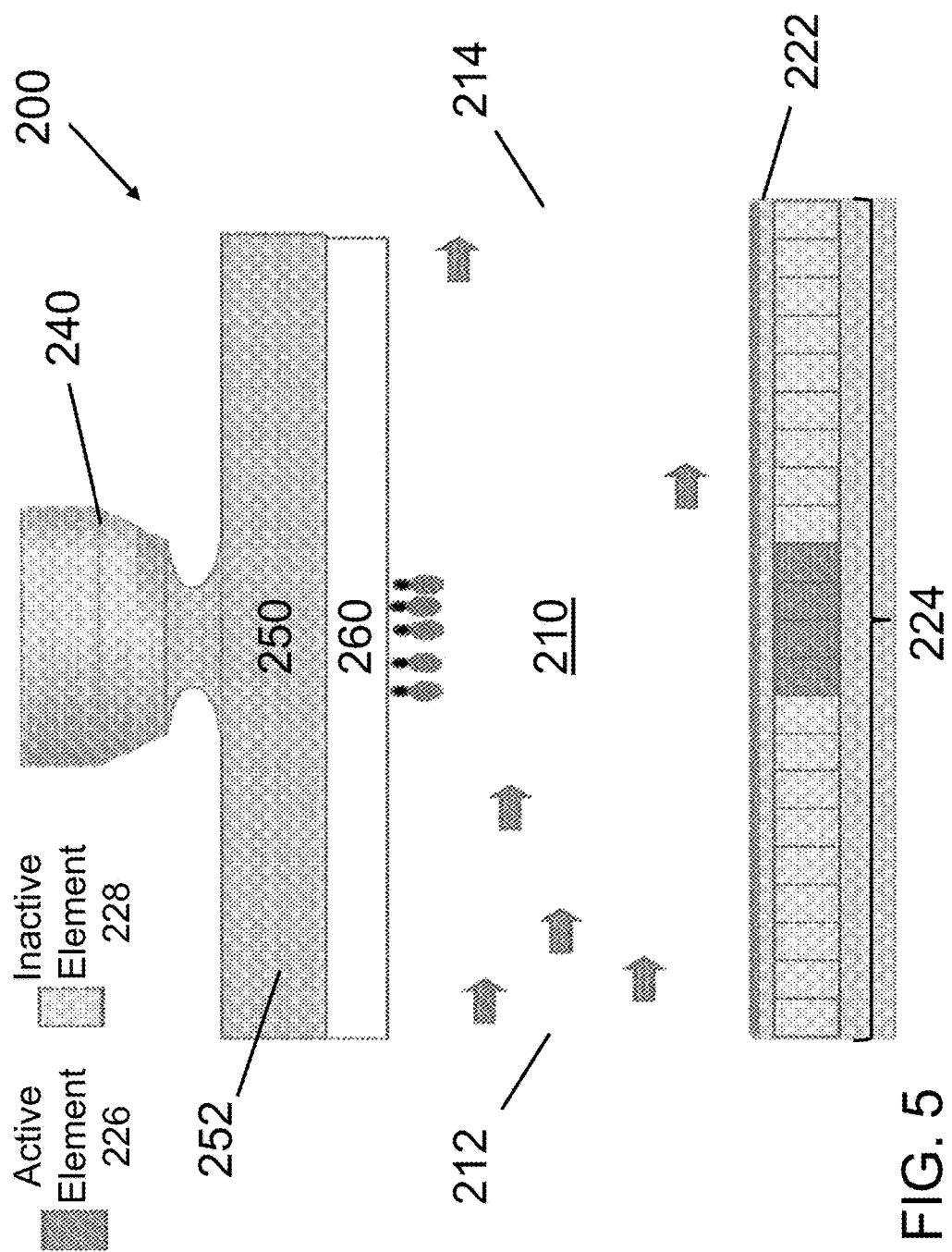
FIG. 5 is a plan view of the acoustophoretic device of FIG. 4. The transducer includes a plurality of piezoelectric elements arranged in an array and configured to operate between active and inactive modes.
Figure 6:
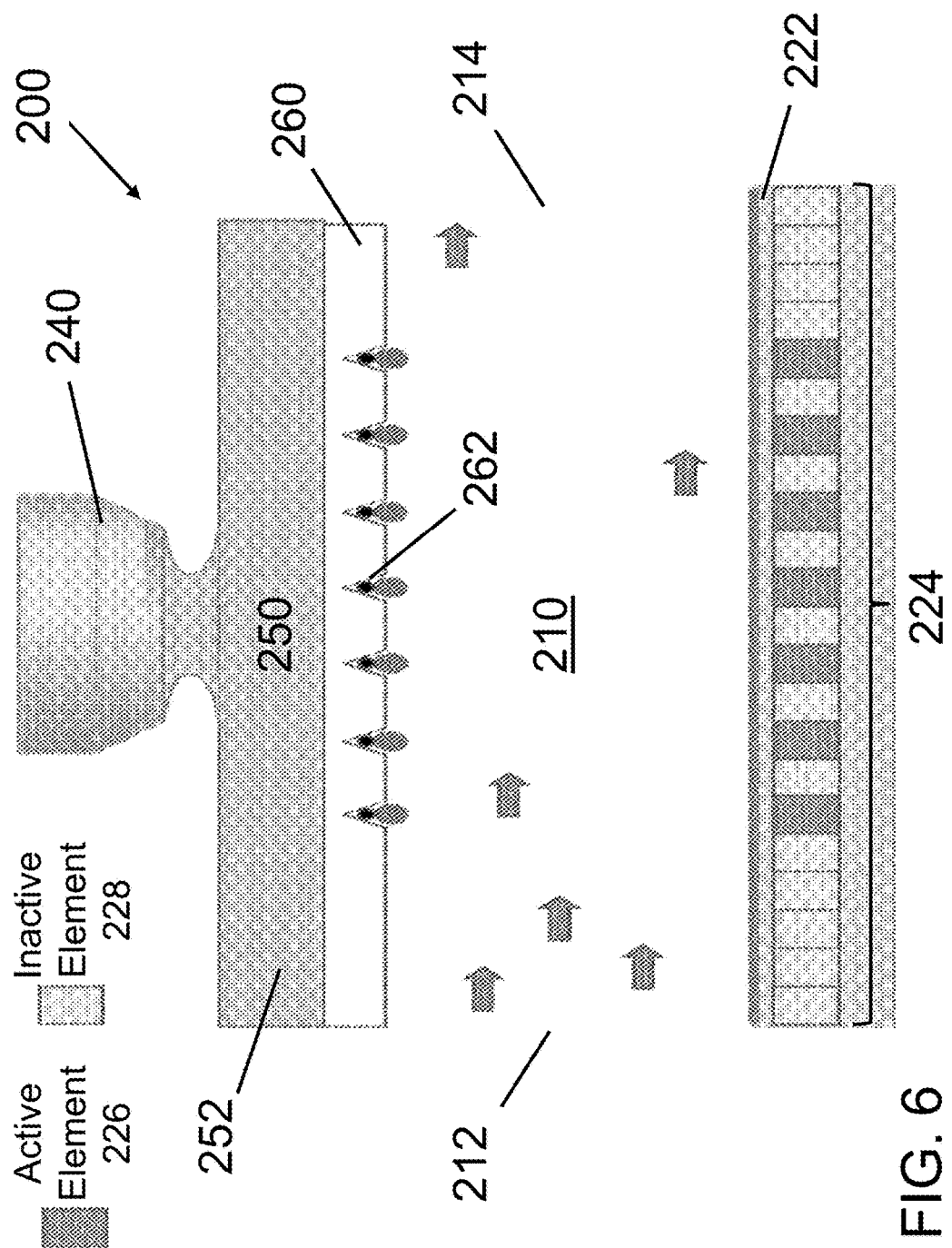
FIG. 6 is a plan view of the acoustophoretic device of FIG. 5. The acoustically transparent layer includes several wells therein, and the piezoelectric elements are switched between active and inactive modes to position targeted cells in the wells.

In accordance with the present disclosure, the acoustophoretic devices described herein, such as that depicted in FIGS. 4-6, can be used for inspecting, detecting, isolating, monitoring, characterizing, or separating various target cells (e.g., specialized circulating cells, such as CTCs, in blood containing blood cells), including their development or interaction with chemicals (e.g., drug candidates).

In the present devices, to isolate specialized circulating cells, paramagnetic particles or hollow microbubbles can be used. The paramagnetic particles/microbubbles generally pull the specialized circulating cells out of the blood because they move in an opposite direction to the blood cells when subjected to acoustophoresis (due to the negative acoustic contrast factor of the paramagnetic particles/microbubbles, which moves towards pressure antinodes of an acoustic standing wave). In this way, microfluidics with sheathing flows and acoustic standing wave(s) can be used to extract and concentrate specialized circulating cells from blood. This provides a distinct advantage over currently-employed systems and methods, which required incubation with immunomagnetic beads to capture magnetically labeled cells by flotation as they passed through isolation zones of known microfluidic devices.

Figure 7:
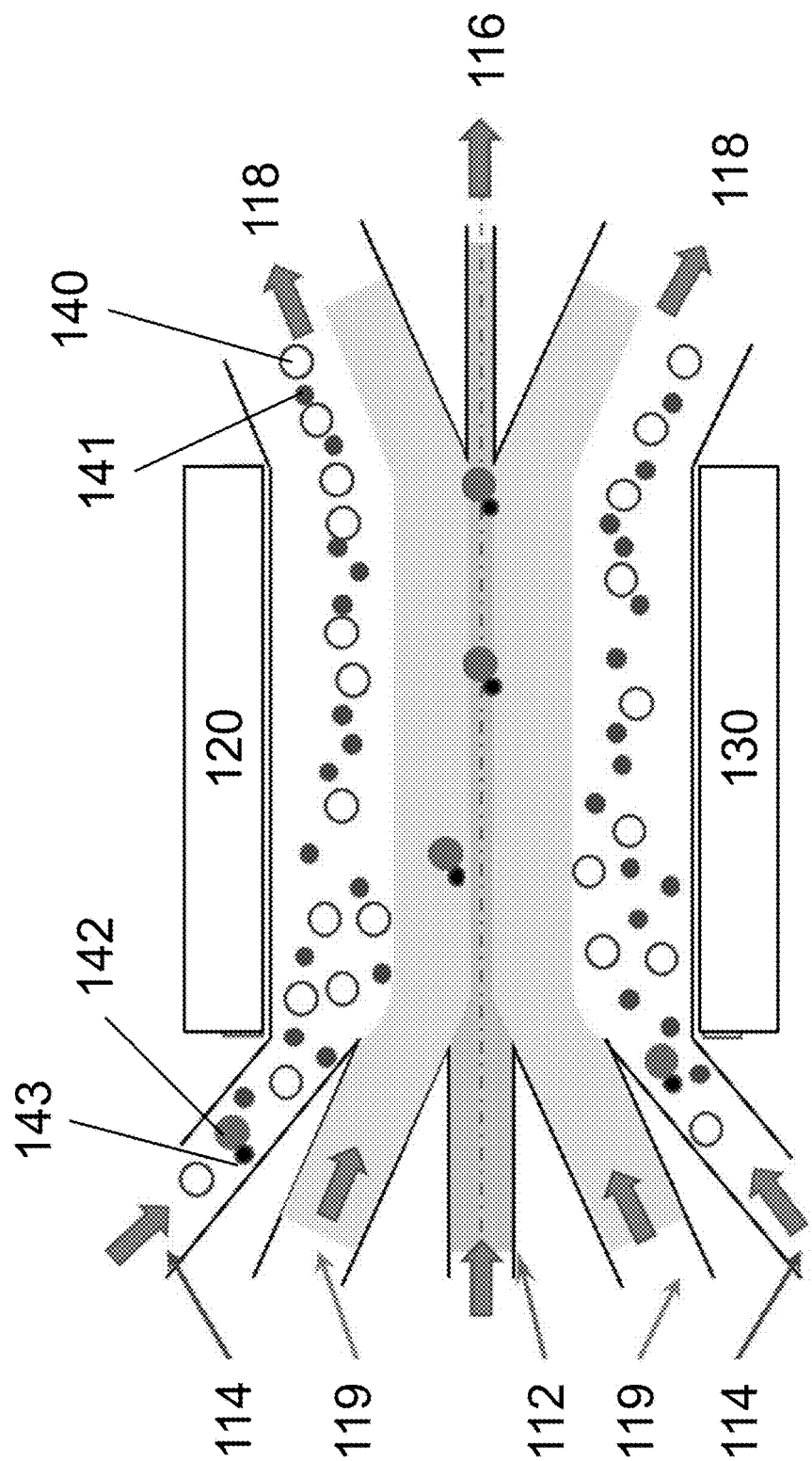
FIG. 7 is a plan view showing one method of the present disclosure. Here, a host fluid is flowed into the flow chamber. Acoustically active particles are attached to target cells. Acoustic standing waves are used to separate the particle-cell complex from the host fluid and other cells, and the particle-cell complex exits from the desired particulate outlet.

This is illustrated in FIG. 7. The system here is similar to that depicted in FIG. 1. As illustrated here, the fluid flowing in through host-fluid inlet 114 contains, for example, cells 140 and 141, the target cells 143, and acoustically active particles 142. The acoustically active particles attach to the target cells. For example, the particles 142 may be coated with an affinity ligand to bind to the target cells 142. The acoustic standing wave generated by transducer 120 and reflector 130 then operate upon the particles 142, resulting in the target cells 143 being separated from the other cells 140, 141. The target cells 143 then exit through the particulate outlet 116, while the other cells 140, 141 exit through the residual outlet 118.

In the presently disclosed acoustophoretic devices, acoustophoresis and acoustically active particles (e.g. microbubbles or paramagnetic particles) can be utilized instead of immunomagnetic beads. For example, device 200 can be operated by flowing blood containing specialized circulating cells and blood cells therethrough and sending a voltage signal to drive the at least one ultrasonic transducer to create the acoustic standing wave in the flow chamber and microbubbles in the blood. Because the device 200 is a one-piece acoustic radiator, the specialized circulating cells with attached microbubbles are driven by the acoustic standing wave toward the acoustically transparent wall where the specialized circulating cells and attached microbubbles become trapped in the acoustic standing wave, such as is depicted in FIG. 3.

With reference to FIG. 5, the piezoelectric material of the ultrasonic transducer 220 may include a plurality of piezoelectric elements 224 arranged in an array. The plurality of piezoelectric elements are configured to operate in active or inactive modes. As explained above, piezoelectric elements in the active mode are generally considered to be "on," such that the specialized circulating cells are trapped above those elements, while elements in the inactive mode are generally considered to be "off," with no trapping of the specialized circulating cells occurring above those elements.

The piezoelectric elements 124 can be individually switched between the active and inactive modes as desired. For example, in FIG. 5, the piezoelectric elements toward the center of the flow chamber 210 are operated in the active mode, and the remaining piezoelectric elements (toward the inlet/outlet of the flow chamber) are operated in the inactive mode. Operating the piezoelectric elements in this way positions the specialized circulating cells trapped in the acoustic standing wave in alignment with the microscope objective 240, which is depicted as being located at or near the center of the flow chamber 210.

Another operation of the piezoelectric elements 124 is depicted in FIG. 6. In FIG. 6, the piezoelectric elements nearest the inlet/outlet of the flow chamber are operated in the inactive mode, and the remaining piezoelectric elements are operated in alternating active/inactive modes. Operating the piezoelectric elements 124 in this way positions the specialized circulating cells trapped in the acoustic standing wave in one or more wells 262 in the acoustically transparent layer 260.

In biological applications, many parts of the device in contact with the sample, e.g. the flow chamber, may all be disposable, with only the transducer and reflector to be cleaned for reuse.

Some further explanation of the ultrasonic transducers used in the devices, systems, and methods of the present disclosure may be helpful as well. In this regard, the transducers use a piezoelectric element, usually made of PZT-8 (lead zirconate titanate). Such elements may have a 1 inch cross-section and a nominal 2 MHz resonance frequency, and may also be of a larger size. Each ultrasonic transducer module can have only one element, or can have multiple elements that each act as a separate ultrasonic transducer and are either controlled by one or multiple amplifiers. The piezoelectric element(s) can be crystalline, semi-crystalline, or non-crystalline. The piezoelectric element(s) can be square, rectangular, irregular polygon, or generally of any arbitrary shape. The transducer(s) is/are used to create a pressure field that generates forces of the same order of magnitude both orthogonal to the standing wave direction (lateral) and in the standing wave direction (axial).

Figure 8:
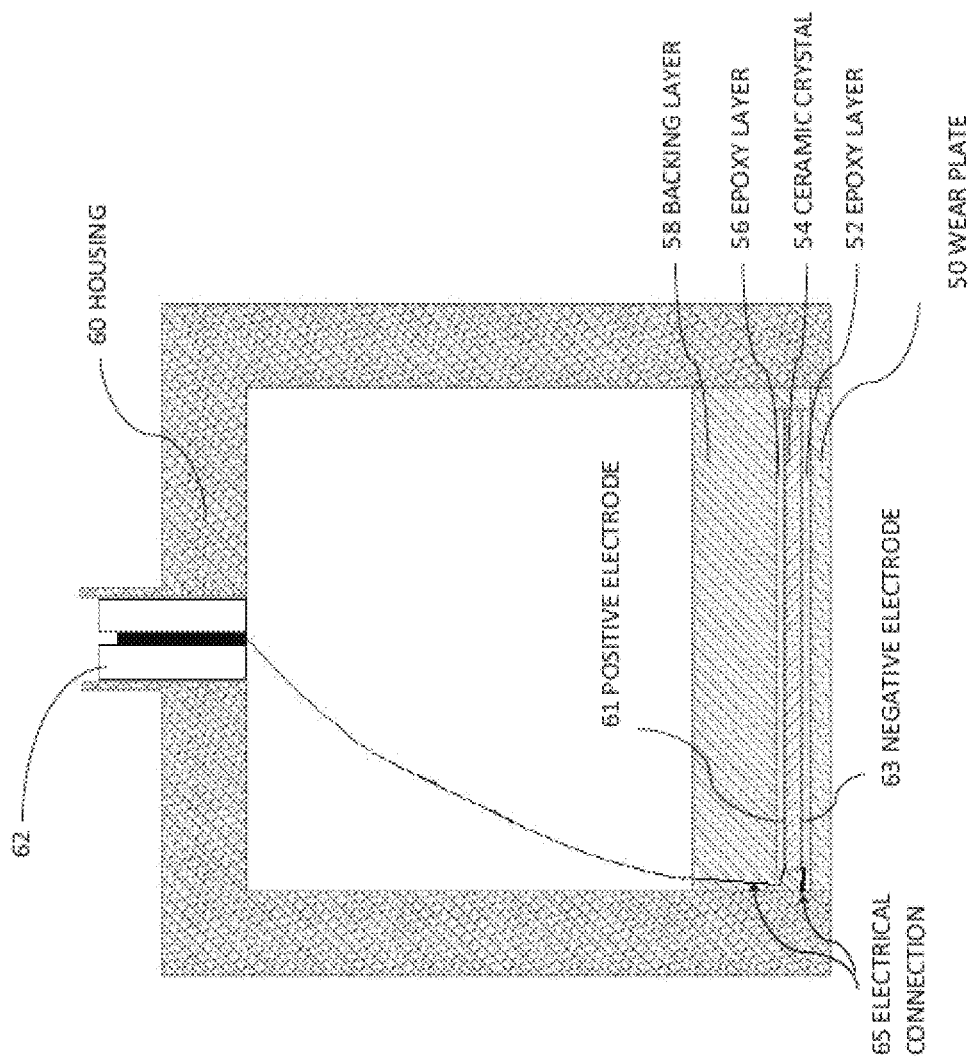
FIG. 8 is a cross-sectional diagram of a conventional ultrasonic transducer.

FIG. 8 is a cross-sectional diagram of a conventional ultrasonic transducer. This transducer has a wear plate 50 at a bottom end, epoxy layer 52, piezoelectric element 54 (e.g. a ceramic crystal made of, e.g. PZT), an epoxy layer 56, and a backing layer 58. On either side of the piezoelectric element, there is an electrode: a positive electrode 61 and a negative electrode 63. The epoxy layer 56 attaches backing layer 58 to the piezoelectric element 54. The entire assembly is contained in a housing 60 which may be made out of, for example, aluminum. An electrical adapter 62 provides connection for wires to pass through the housing and connect to leads (not shown) which attach to the piezoelectric element 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

Figure 9:
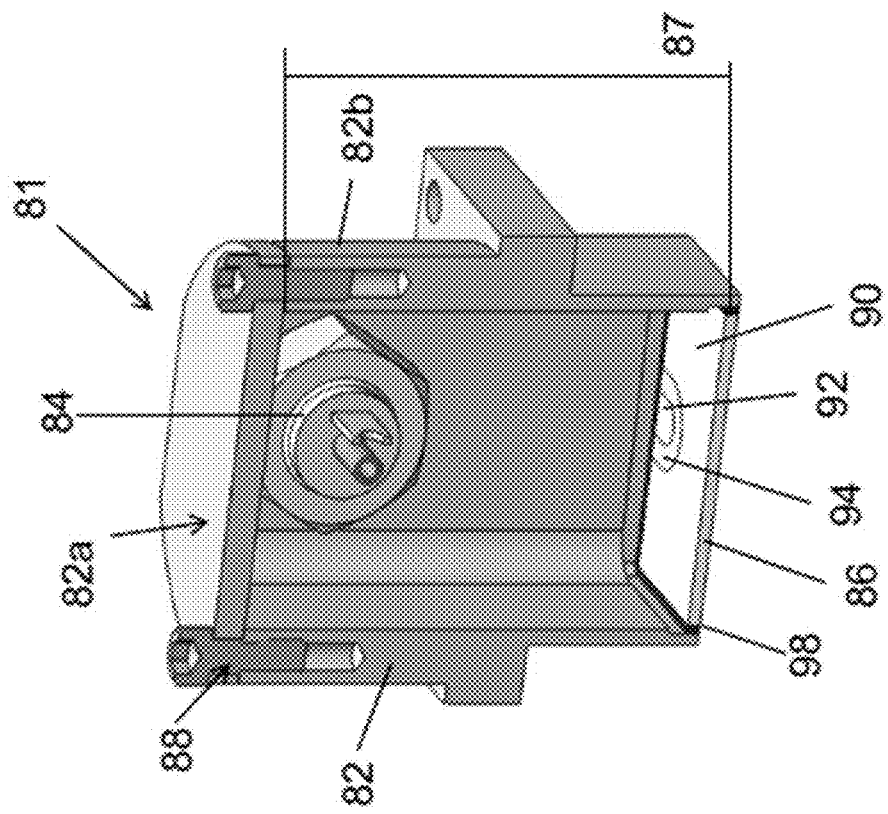
FIG. 9 is a cross-sectional diagram of an ultrasonic transducer according to the present disclosure. An air gap is present within the transducer, and no backing layer or wear plate is present.

FIG. 9 is a cross-sectional view of an ultrasonic transducer 81 of the present disclosure. Transducer 81 is shaped as a disc or a plate, and has an aluminum housing 82. The piezoelectric element can be, e.g., a mass of perovskite ceramic crystals, each consisting of a small, tetravalent metal ion, usually titanium or zirconium, in a lattice of larger, divalent metal ions, usually lead or barium, and O2− ions. As an example, in the embodiment shown in FIG. 9, a PZT (lead zirconate titanate) crystal 86 defines the bottom end of the transducer, and is exposed from the exterior of the housing. The crystal is supported on its perimeter by a small elastic layer 98, e.g. silicone or similar material, located between the crystal and the housing. Put another way, no wear layer is present. In particular embodiments, the crystal is an irregular polygon, and in further embodiments is an asymmetrical irregular polygon.

Figure 10:
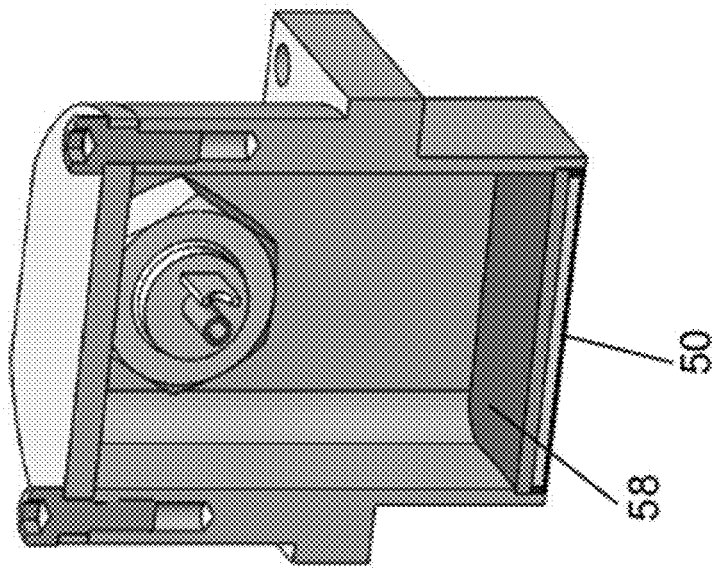
FIG. 10 is a cross-sectional diagram of an ultrasonic transducer according to the present disclosure. An air gap is present within the transducer, and a backing layer and wear plate are present.

Screws 88 attach an aluminum top plate 82a of the housing to the body 82b of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer. Put another way, there is an air gap 87 in the transducer between aluminum top plate 82a and the crystal 86 (i.e. the air gap is completely empty). A minimal backing 58 and/or wear plate 50 may be provided in some embodiments, as seen in FIG. 10.

The transducer design can affect performance of the system. A typical transducer is a layered structure with the piezoelectric element bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the piezoelectric element to vibrate in one of its eigenmodes (i.e. near eigenfrequency) with a high Q-factor. The vibrating piezoelectric element, such as, e.g., a ceramic crystal/disk, is directly exposed to the fluid flowing through the acoustic chamber.

Removing the backing (e.g. making the piezoelectric element air backed) also permits the element to vibrate at higher order modes of vibration with little damping (e.g. higher order modal displacement). In a transducer having a piezoelectric element with a backing, the element vibrates with a more uniform displacement, like a piston. Removing the backing allows the element to vibrate in a non-uniform displacement mode. The higher order the mode shape of the piezoelectric element, the more nodal lines the element has. The higher order modal displacement of the element creates more trapping lines, although the correlation of trapping line to node is not necessarily one to one, and driving the element at a higher frequency will not necessarily produce more trapping lines.

In some embodiments, the piezoelectric element may have a backing that minimally affects the Q-factor of the crystal (e.g. less than 5%). The backing may be made of a substantially acoustically transparent material such as balsa wood, foam, or cork which allows the element to vibrate in a higher order mode shape and maintains a high Q-factor while still providing some mechanical support for the element. The backing layer may be a solid, or may be a lattice having holes through the layer, such that the lattice follows the nodes of the vibrating element in a particular higher order vibration mode, providing support at node locations while allowing the rest of the element to vibrate freely. The goal of the lattice work or acoustically transparent material is to provide support without lowering the Q-factor of the piezoelectric element or interfering with the excitation of a particular mode shape.

Placing the piezoelectric element in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymers or polymer films. Organic and biocompatible coatings such as silicone or polyurethane are also usable as a wear surface.

Certain embodiments of the acoustophoretic devices and methods described herein are useful for preparing a sample for subsequent downstream processing. In this regard, the sample may be subsequently processed by any known filtration or processing, such as by using a portable flow cytometer. Other embodiments of the acoustophoretic devices and methods described herein are useful for inspecting, detecting, isolating, or characterizing bacteria or specialized circulating cells in blood containing blood cells. In this regard, the bacteria or specialized circulating cells may be subsequently processed or filtered by any known filtration or processing, such as by collecting the bacteria or specialized circulating cells from the device and feeding the same to another filtration process.

Avoiding centrifuges and physical filters allows better separation of cells without lowering the viability of the cells. The form factor of the acoustophoretic device is also smaller than a physical filtration system, allowing cell separation to be miniaturized. The transducers may also be driven to create rapid pressure changes to prevent or clear blockages due to agglomeration of cells. The frequency of the transducers may also be varied to obtain optimal effectiveness for a given power.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method for inspecting, detecting, isolating, monitoring, characterizing, or separating target cells in a host fluid also containing non-target cells, the method comprising:
   flowing the host fluid containing the target cells and the non-target cells through an acoustophoretic device, the acoustophoretic device comprising:
      a flow chamber including a solvent inlet and at least one host-fluid inlet at a first end of the flow chamber, and a particulate outlet and at least one residual outlet at a second end of the flow chamber opposite the first end thereof, wherein the solvent inlet and the particulate outlet are aligned with a longitudinal axis of the flow chamber and the at least one host-fluid inlet and the at least one residual outlet are spaced apart from the longitudinal axis;
      at least one ultrasonic transducer coupled to the flow chamber, the at least one ultrasonic transducer including a piezoelectric material configured to be excited to generate an acoustic standing wave in the flow chamber; and
      a reflector across the flow chamber from the at least one ultrasonic transducer;
   exciting the at least one ultrasonic transducer to create the acoustic standing wave in the flow chamber to drive the target cells toward the longitudinal axis where the target cells become trapped in the acoustic standing wave;
   attaching acoustically active particles to the target cells;
   introducing a solvent into the flow chamber through the solvent inlet; and
   removing the target cells from the device through the particulate outlet.

2. The method of claim 1, wherein the acoustophoretic device further comprises at least one buffer inlet located between the solvent inlet and the at least one host-fluid inlet.

3. The method of claim 2, further comprising introducing a buffer into the flow chamber through the at least one buffer inlet, the buffer creating a buffer layer that permits the target cells to pass therethrough but destroys the non-target cells as they pass therethrough.

4. The method of claim 3, wherein the buffer is a selective lytic buffer.

5. The method of claim 1, further comprising removing a portion of the solvent from the device through the residual outlet.

6. The method of claim 1, wherein the piezoelectric material includes a plurality of piezoelectric elements arranged in an array, the plurality of piezoelectric elements operated between active and inactive modes such that the target cells are trapped above the piezoelectric elements in the active mode.

7. The method of claim 6, further comprising switching the piezoelectric elements between the active and inactive modes to move the target cells trapped in the acoustic standing wave along the longitudinal axis from the first end to the second end of the flow chamber to the particulate outlet.

8. The method of claim 1, wherein the solvent is a bacteria-friendly solvent.

9. The method of claim 1, wherein the acoustic standing wave is a multi-dimensional acoustic standing wave.

10. An acoustophoretic device, comprising:
    a flow chamber that includes a solvent inlet and at least one host-fluid inlet at a first end of the flow chamber, a buffer inlet located between the solvent inlet and the at least one host-fluid inlet, and a particulate outlet and at least one residual outlet at a second end of the flow chamber opposite the first end thereof, wherein the solvent inlet and the particulate outlet are aligned with a longitudinal axis of the flow chamber and the at least one host-fluid inlet and the at least one residual outlet are spaced apart from the longitudinal axis;
    at least one ultrasonic transducer coupled to the flow chamber, the at least one ultrasonic transducer including a piezoelectric material configured to be excited to generate an acoustic standing wave in the flow chamber; and
    a reflector across the flow chamber from the at least one ultrasonic transducer.

11. The acoustophoretic device of claim 10, wherein the piezoelectric material includes a plurality of piezoelectric elements arranged in an array, the plurality of piezoelectric elements configured to operate between active and inactive modes.

12. The acoustophoretic device of claim 10, wherein the flow chamber is disposable.

13. The acoustophoretic device of claim 10, wherein the at least one ultrasonic transducer comprises:
    a housing having a top end, a bottom end, and an interior volume; and
    a piezoelectric crystal at the bottom end of the housing having an exposed exterior surface and an interior surface, the crystal being able to vibrate when driven by a voltage signal.

14. The acoustophoretic device of claim 13, wherein no backing layer is present within the housing of the at least one ultrasonic transducer, and an air gap is present in the interior volume between the crystal and a top plate at the top end of the housing; or
    wherein the at least one ultrasonic transducer further comprises a backing layer contacting the interior surface of the crystal, the backing layer being made of a substantially acoustically transparent material.

15. A method for inspecting, detecting, isolating, monitoring, characterizing, or separating specialized circulating cells in blood containing blood cells, the method comprising:
    flowing the blood containing specialized circulating cells and blood cells through an acoustophoretic device, the acoustophoretic device comprising:
        a flow chamber that includes at least one inlet and at least one outlet;
        at least one ultrasonic transducer coupled to the flow chamber, the at least one ultrasonic transducer including a piezoelectric material configured to be excited to generate an acoustic standing wave in the flow chamber; and a cover glass forming a wall of the flow chamber opposite the at least one ultrasonic transducer;

exciting the at least one ultrasonic transducer to create the acoustic standing wave in the flow chamber and microbubbles in the blood, the microbubbles attaching to the specialized circulating cells and being driven by the acoustic standing wave toward the cover glass where the specialized circulating cells and attached microbubbles become trapped in the acoustic standing wave; and examining the specialized circulating cells using a microscope objective.

16. The method of claim 15, wherein the at least one inlet includes a solvent inlet and at least one host-fluid inlet at a first end of the flow chamber, and the at least one outlet includes a particulate outlet and at least one residual outlet at a second end of the flow chamber opposite the first end thereof, wherein the solvent inlet and the particulate outlet are aligned with a longitudinal axis of the flow chamber and the at least one host-fluid inlet and the at least one residual outlet are spaced apart from the longitudinal axis.

17. The method of claim 16, wherein the acoustophoretic device further comprises at least one buffer inlet located between the solvent inlet and the at least one host-fluid inlet.

18. The method of claim 17, further comprising introducing a dividing buffer into the flow chamber through the at least one buffer inlet.

19. The method of claim 15, wherein the acoustophoretic device further comprises a substantially acoustically transparent layer between the cover glass and the flow chamber.

20. The method of claim 19, wherein the piezoelectric material includes a plurality of piezoelectric elements arranged in an array, the plurality of piezoelectric elements operated between active and inactive modes such that the specialized circulating cells are trapped above the piezoelectric elements in the active mode.

21. The method of claim 20, further comprising switching the piezoelectric elements between the active and inactive modes to position the specialized circulating cells trapped in the acoustic standing wave in alignment with the microscope objective.

22. The method of claim 20, wherein the substantially acoustically transparent layer includes one or more wells therein.

23. The method of claim 22, further comprising switching the piezoelectric elements between the active and inactive modes to position the specialized circulating cells trapped in the acoustic standing wave in in the one or more wells.

24. The method of claim 15 wherein the specialized circulating cells are circulating tumor cells.

25. The method of claim 15, wherein the acoustic standing wave is a multi-dimensional acoustic standing wave.

26. An acoustophoretic device, comprising:

a flow chamber that includes at least one inlet and at least one outlet;

at least one ultrasonic transducer coupled to the flow chamber, the at least one ultrasonic transducer including a piezoelectric material configured to be excited to generate an acoustic standing wave in the flow chamber;

the piezoelectric material includes a plurality of piezoelectric elements arranged in an array, the plurality of piezoelectric elements configured to operate between active and inactive modes; and the flow chamber including an optically transparent wall opposite the at least one ultrasonic transducer.

27. The acoustophoretic device of claim 26, wherein the at least one inlet includes a solvent inlet and at least one host-fluid inlet at a first end of the flow chamber, and the at least one outlet includes a particulate outlet and at least one residual outlet at a second end of the flow chamber opposite the first end thereof, wherein the solvent inlet and the particulate outlet are aligned with a longitudinal axis of the flow chamber and the at least one host-fluid inlet and the at least one residual outlet are spaced apart from the longitudinal axis.

28. The acoustophoretic device of claim 27, further comprising at least one buffer inlet located between the solvent inlet and the at least one host-fluid inlet.

29. The acoustophoretic device of claim 27, further comprising an acoustic concentrator fluidly connected to the particulate outlet.

30. The acoustophoretic device of claim 26, further comprising a substantially acoustically transparent layer between the optically transparent wall and the flow chamber.

31. The acoustophoretic device of claim 30, wherein the substantially acoustically transparent layer includes one or more wells therein.

32. The acoustophoretic device of claim 26, wherein the flow chamber is disposable.

33. The acoustophoretic device of claim 26, wherein the at least one ultrasonic transducer comprises:

a housing having a top end, a bottom end, and an interior volume; and a piezoelectric crystal at the bottom end of the housing having an exposed exterior surface and an interior surface, the crystal being able to vibrate when driven by a voltage signal.

34. The acoustophoretic device of claim 33, wherein no backing layer is present within the housing of the at least one ultrasonic transducer, and an air gap is present in the interior volume between the crystal and a top plate at the top end of the housing.

35. The acoustophoretic device of claim 33, wherein the at least one ultrasonic transducer further comprises a backing layer contacting the interior surface of the crystal, the backing layer being made of a substantially acoustically transparent material.

* * * * *